United States Patent
Musa et al.

(10) Patent No.: US 9,445,999 B2
(45) Date of Patent: *Sep. 20, 2016

(54) PROCESS FOR PREPARING CARRIER PARTICLES FOR DRY POWDERS FOR INHALATION

(71) Applicant: CHIESI FARMACEUTICI S.p.A., Parma (IT)

(72) Inventors: Rossella Musa, Parma (IT); Daniela Cocconi, Parma (IT); Alain Chamayou, Parma (IT); Laurence Galet, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/607,289

(22) Filed: Jan. 28, 2015

(65) Prior Publication Data

US 2015/0202159 A1    Jul. 23, 2015

Related U.S. Application Data

(63) Continuation of application No. 13/078,057, filed on Apr. 1, 2011, now Pat. No. 8,974,831.

(30) Foreign Application Priority Data

Apr. 1, 2010    (EP) .................................... 10158951

(51) Int. Cl.
| | | |
|---|---|---|
| *A61K 31/167* | (2006.01) | |
| *A61K 31/40* | (2006.01) | |
| *A61K 31/57* | (2006.01) | |
| *A61K 9/16* | (2006.01) | |
| *A61K 9/00* | (2006.01) | |
| *A61K 9/50* | (2006.01) | |
| *A61K 9/14* | (2006.01) | |

(52) U.S. Cl.
CPC ........... *A61K 9/1682* (2013.01); *A61K 9/0075* (2013.01); *A61K 9/145* (2013.01); *A61K 9/5015* (2013.01); *A61K 31/167* (2013.01); *A61K 31/40* (2013.01); *A61K 31/57* (2013.01)

(58) Field of Classification Search
CPC ........... A61K 2300/00; A61K 9/5036; A61K 45/06; A61K 9/5161; A61K 9/14; A61K 9/1652; A61K 33/26; A61K 9/5078; A61K 47/36; A61K 47/4823; A61K 9/5073; A61K 9/5026; A61K 9/5089; A61K 33/30; A61K 41/00

See application file for complete search history.

(56) References Cited

U.S. PATENT DOCUMENTS

| | | |
|---|---|---|
| 6,645,466 B1 | 11/2003 | Keller et al. |
| 6,780,508 B1 | 8/2004 | Caponetti et al. |
| 2005/0220996 A1 | 10/2005 | Berger et al. |

FOREIGN PATENT DOCUMENTS

| | | |
|---|---|---|
| EP | 2 080 508 | 7/2009 |
| WO | 00/53157 | 9/2000 |
| WO | 2005/105043 | 11/2005 |
| WO | 2009/001064 | 12/2008 |

OTHER PUBLICATIONS

European Search Report in Application No. 10158951.3, issued Oct. 20, 2010.
Zhou Qi Tony et al., "European Journal of Pharmaceutical Sciences", vol. 40, No. 5 (2010) pp. 412-421.
Kumon, Michiko et al., "Chemical & Pharmaceutical Bulletin", vol. 56, No. 5 (2008) pp. 617-625.
"Particle and Powder Flow Properties—Part II", Rajesh N. Dave, NJ Center for Engineered Particulates, Accessed online Jun. 11, 2014.

*Primary Examiner* — Audrea Buckley
(74) *Attorney, Agent, or Firm* — Oblin, McClelland, Maier & Neustadt, L.L.P

(57) ABSTRACT

Carrier particles in which at least 60% of the surface is coated with magnesium stearate are useful for preparing dry powder formulations for inhalation.

18 Claims, 3 Drawing Sheets

Magnification: 200 microns

Magnification: 500 microns

Magnification: 500 microns

Magnification: 100 microns (x2)

Magnification: 100 microns (x5)

Magnification: 100 microns (x5)

PROCESS FOR PREPARING CARRIER PARTICLES FOR DRY POWDERS FOR INHALATION

This is a Continuation Application of U.S. patent application Ser. No. 13/078,057, filed on Apr. 1, 2011, now U.S. Pat. No. 8,974,831, and claims priority to European Patent Application No. 10158951.3 filed on Apr. 1, 2010, which is incorporated herein by reference in its entirety.

CROSS REFERENCES TO RELATED APPLICATIONS

This application claims priority to European Patent Application No. 10158951.3 filed on Apr. 1, 2010, which is incorporated herein by reference in its entirety.

BACKGROUND OF THE INVENTION

1. Field of the Invention

The present invention relates to processes for preparing carrier particles for use in dry powder formulations for inhalation. The present invention also relates to carrier particles produced by such a process and dry powder formulations prepared with such carrier particles. The present invention further relates to methods for the treatment and/or prevention of certain diseases and conditions by administering such a dry powder formulation.

2. Discussion of the Background

Dry powder inhalation (DPI) drug therapy has been used for many years to treat respiratory conditions such as asthma, chronic obstructive pulmonary disease (COPD), and allergic rhinitis. Compared to oral drug intake, only relatively small doses are needed for effective therapy as first pass metabolism is significantly reduced. Such small doses reduce the body's exposure to the drug and minimize side effects. Systemic adverse effects are also reduced as topical lung delivery takes the drug directly to the site of action. Lower dosage regimens may also provide considerable cost savings, particularly where expensive therapeutic agents are concerned.

Dry powder forms are typically formulated by mixing the drug in micronized form with coarse carrier particles, giving rise to an ordered mixture where the micronized active particles adhere to the surface of the carrier particles whilst in the inhaler device. The carrier makes the micronized powder less cohesive and improves its flowability, making it easier to handle the powder during the manufacturing process (pouring, filling, etc.).

During inhalation, the drug particles separate from the surface of carrier particles and penetrate into the lower lungs, while the larger carrier particles are mostly deposited in the oropharyngeal cavity.

The re-dispersion of drug particles from the carrier surface is regarded as the most critical factor which governs the availability of the medicament to the lungs. This will depend on the mechanical stability of the powder mix and the way this is influenced by the adhesion characteristics between the drug and the carrier and the external forces required to break up the non covalent bonds formed between adhering particles. Too strong bonds between adhering particles may indeed prevent the separation of the micronized drug particles from the surface of carrier particles.

Different approaches aimed at modulating the adhesion have been proposed in the art to promote the release of the drug particles from the carrier particles and, hence, to increase the respirable fraction. For example, the use of additives with lubricant or anti-adherent properties has been suggested as a solution of the technical problem. A particularly useful additive has been found to be magnesium stearate.

The benefit of using magnesium stearate in dry powders is taught in U.S. Pat. No. 6,528,096, which is incorporated herein by reference in its entirety. Specifically, it discloses that said additive can be used to alter the surface properties of carrier particles and thereby improve the properties of dry powder formulations. U.S. Pat. No. 6,528,096 discloses an "advantageous relationship" between surface coating carrier particles with magnesium stearate and the fine particle fraction (respirable fraction) of the emitted dose. Critical to the working of this effect is the need to ensure a coating of magnesium stearate over more than 15% of the surface of the carrier particles. In the examples of U.S. Pat. No. 6,528,096, percentages of coating up to 38% are disclosed.

However it would be highly advantageous to provide a process capable of giving rise to higher percentages of surface coating, as it would allow the improvement of the performances of the formulation by using a lower amount of additive.

SUMMARY OF THE INVENTION

Accordingly, it is one object of the present invention to provide novel processes for preparing carrier particles for use in dry powder formulations for inhalation.

It is another object of the present invention to provide novel carrier particles produced by such a process.

It is another object of the present invention to provide novel dry powder formulations prepared with such carrier particles.

It is another object of the present invention to provide novel methods for the treatment and/or prevention of certain diseases and conditions by administering such a dry powder formulation.

These and other objects, which will become apparent during the following detailed description, have been achieved by the inventors' discovery that improved carrier particles may be obtained by a process which comprises subjecting particles made of lactose to dry coating with magnesium stearate to provide a surface coating of the lactose particles, wherein said dry coating is carried out in a high shear mixer granulator based on friction behavior.

Thus, in a first aspect, the present invention provides a process for the preparation of a carrier for powder pharmaceutical compositions for inhalation, the process comprising subjecting particles made of lactose having a mass diameter in the range 30 to 1000 microns to dry coating with 0.1 to 1.3% magnesium stearate by weight of the carrier, to provide a surface coating of the lactose particles with said magnesium stearate to an extent such that the coated particles have more than 60% of surface coating, wherein the dry coating step is carried out in a high shear mixer granulator based on friction behavior, at a rotation speed equal to or higher than 500 r.p.m, preferably equal to or higher than 1000 r.p.m., but equal to or lower than 2500 r.p.m, preferably lower than 2000 r.p.m.

Preferably, said high shear mixer granulator is the CYCLOMIX™ apparatus.

In a second aspect, the present invention provides carrier particles for dry powder formulations for inhalation, said carrier particles comprising particles of lactose having a mass diameter in the range 30 to 1000 microns coated with 0.1 to 1.3% magnesium stearate by weight of the carrier, to an extent such that the coated particles have more than 60% of surface coating, said carrier particles being obtainable by a process which comprises the step of dry coating in a high shear mixer granulator based on friction behavior between the aforementioned lactose particles and magnesium stearate at a rotation speed equal to or higher than 500 r.p.m, preferably equal to or higher than 1000 r.p.m, but equal to or lower than 2500 r.p.m, preferably lower than 2000 r.p.m.

In a third aspect, the present invention provides carrier particles for dry powder formulations for inhalation, said carrier particles comprising particles of lactose having a mass diameter in the range 30 to 1000 microns coated with 0.1 to 1.3% magnesium stearate by weight of the carrier to an extent such that the coated particles have more than 60% of surface coating.

In a fourth aspect, the present invention provides a pharmaceutical composition in the form of a dry powder for inhalation comprising the carrier particles of the present invention and one or more active ingredients.

In a fifth aspect, the present invention provides a dry powder inhaler filled with the aforementioned dry powder pharmaceutical composition.

In a sixth aspect, the present invention provides a process for preparing the aforementioned pharmaceutical composition comprising a step of mixing the carrier particles of the present invention with one or more active ingredient.

In a further aspect, the present invention is also directed to a package comprising a dry powder pharmaceutical formulation according to the present invention and a dry powder inhaler.

In yet another aspect the present invention provides methods for the treatment and/or prevention of certain diseases and conditions by administering the aforementioned dry powder pharmaceutical composition.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Unless otherwise specified, the terms "active drug," "active ingredient," "active," "active substance," "active compound," and "therapeutic agent" are used synonymously.

The expression "high shear mixer granulator based on friction behavior" refers to an apparatus fitted with paddle shape mixing elements wherein the particles are accelerated by the paddles and intensively mixed by the friction against the vessel wall.

The term "dry coating" refers to a mechanical process wherein a first material (i.e. magnesium stearate) form a physical interaction (coating) with a second material (i.e. carrier) in dry conditions, e.g. without solvents, binders or water.

Figure 1:
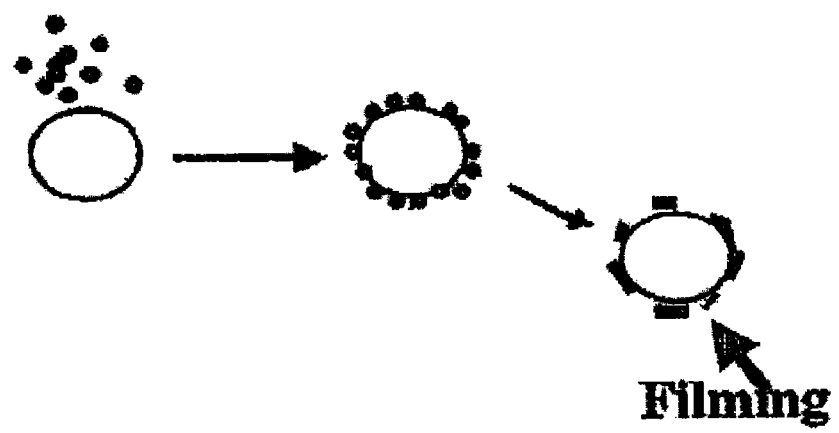
FIG. 1 is a scheme of the film forming process around a single carrier particle.
Figure 2A:
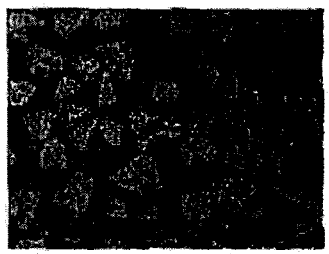
FIG. 2A, FIG. 2B, FIG. 2C, FIG. 2D, FIG. 2E, and FIG. 2F show SEM pictures at different magnifications of: lactose particles+0.5% magnesium stearate at 1500 r.p.m. for 5 minutes (6.5×, top left; 6.5×, bottom left); lactose particles+0.5% magnesium stearate at 1500 r.p.m. for 10 minutes (6.5×, top middle; 6.5×, bottom middle); lactose particles+0.5% magnesium stearate at 1500 r.p.m. for 15 minutes (6.5×, top right; 6.5×, bottom right)
Figure 2B:
Figure 2C:
Figure 2D:
Figure 2E:
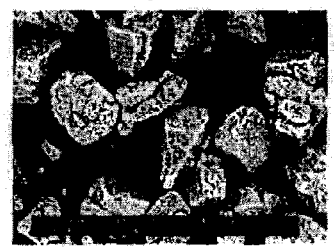
Figure 2F:

The term "surface coating" refers to the covering of the surface of the carrier particles by forming a film of magnesium stearate around said particles as reported in the diagram shown in FIG. 1. The thickness of the film has been estimated by X-ray photoelectron spectroscopy (XPS) to be approximately of less than 10 nm.

The percentage of surface coating indicates the extent by which magnesium stearate coats the surface of all the carrier particles.

From all of the above, it is clear to the skilled person that, in the coating according to the present invention, at least 60% of the whole surface of the carrier particles are coated.

The term "hygroscopic" refers to an active compound that never completely dries in contact with air having a moisture content of >0% relative humidity, but always contains a certain amount of absorptively bound water (see, H. Sucker, P. Fuchs and P. Speiser: *Pharmaceutical Technology*, Georg Thieme Verlag, Stuttgart, New York, 2nd edition 1991, page 85, which is incorporated herein by reference).

The term "hydrophilic" refers to an active compound that can easily be wetted by water. For instance formoterol is a typical hydrophilic active ingredient.

In general terms, the particle size of the particles is quantified by measuring a characteristic equivalent sphere diameter, known as volume diameter, by laser diffraction.

The particle size can also be quantified by measuring the mass diameter by means of suitable instruments and techniques known to the skilled person, such as sieving.

The volume diameter (VD) is related to the mass diameter (MD) by the density of the particles (assuming the size being independent from the density of the particles).

In the present application, the particle size interval is expressed in terms of mass diameter. Otherwise, the particle size distribution is expressed in terms of: i) the volume median diameter (VMD) which corresponds to the diameter of 50 percent by weight or volume respectively, of the particles, e.g. d(v0.5); and ii) the volume diameter (VD) in microns of 10% and 90% of the particles, respectively, e.g. d(v0.1) and d(v0.9).

The term "good flow properties" refers to a formulation that is easy handled during the manufacturing process and is capable of ensuring an accurate and reproducible delivery of the therapeutically effective dose.

Flow characteristics can be evaluated by measuring the Carr's index; a Carr's index of less than 25 is usually taken to indicate good flow characteristics.

The expression "good homogeneity" refers to a formulation wherein, upon mixing, the content uniformity of the active ingredient, expressed as relative standard deviation (RSD), is less than 5%, preferably equal to or less than 2.5%.

The expression "physically stable in the device before use" refers to a formulation wherein the active particles do not substantially segregate and/or detach from the surface of the carrier particles both during manufacturing of the dry powder and in the delivery device before use. The tendency to segregate can be evaluated according to Staniforth et al., *J. Pharm. Pharmacol.*, vol. 34, pp. 700-706 (1982), which is incorporated herein by reference in its entirety, and it is considered acceptable if the distribution of the active ingredient in the powder formulation after the test, expressed as relative standard deviation (RSD), does not change significantly with respect to that of the formulation before the test.

The expression "respirable fraction" refers to an index of the percentage of active ingredient particles which would reach the deep lungs in a patient. The respirable fraction, also termed fine particle fraction (FPF), is commonly evaluated using a suitable in vitro apparatus, typically the Multistage Cascade Impactor or Multi Stage Liquid Impinger (MLSI) according to procedures reported in common Pharmacopoeias. It is calculated by the ratio between the respirable dose and the delivered (emitted) dose. The delivered dose is calculated from the cumulative deposition in the apparatus, while the respirable dose (fine particle dose) is calculated from the deposition on Stages 3 (S3) to filter (AF) corresponding to particles≤4.7 microns.

A respirable fraction higher than 30% is an index of good inhalatory performances.

The term "therapeutic amount" means the amount of active ingredient that when delivered to the lungs via a dry powder formulation as described herein provides the desired biological effect.

By "single dose" it is meant the quantity of active ingredient administered at one time by inhalation upon actuation of the inhaler.

By "actuation" it is meant the release of active ingredient from the device by a single activation (e.g. mechanical or breath).

The present invention is directed to processes for the preparation of a carrier for powder pharmaceutical compositions for inhalation, the process comprising subjecting particles made of lactose to dry coating with magnesium stearate to provide a surface coating of the lactose particles, wherein said dry coating is carried out in a high shear mixer granulator based on friction behavior.

It has been found that by using this kind of apparatus wherein the particles are subjected to friction forces, the occurrence of breakage of the carrier particles is less probable than in other apparatus such as those based on impact forces.

Magnesium stearate is an additive with lubricant properties that is mainly used for increasing the respirable fraction of the active ingredient.

Ant type of magnesium stearate of pharmaceutical grade commercially available, may be used, despite of its origin.

The amount of magnesium stearate should be 0.1 to 1.3% by weight based on the weight of the carrier in such a way that the relevant formulation retains its homogeneity during conditions that are comparable to those that might occur during commercial processing.

Advantageously, the amount of magnesium stearate may be 0.15 to 1.0% by weight (w/w).

Within these limits, the amount of magnesium stearate will depend on both the dry powder inhaler and the active ingredient employed in the powder formulation. The skilled person will have an understanding of the physical and chemical properties of the active ingredient and the type of inhaler, for example single dose or multidose, and be able to select an appropriate amount.

In one embodiment of the present invention, the amount of magnesium stearate may 0.15 to 0.5% w/w, more preferably 0.2 to 0.4% w/w, or 0.1 to 0.3% w/w, based on the weight of the carrier. In other embodiments, it may be 0.3 to 0.5% w/w or 0.4 to 1.0% w/w, more preferably 0.5 to 0.8% by weight based on the weight of the carrier. In further embodiments, it may be 0.65 to 1.25% w/w, preferably 0.7 to 1.1% w/w, based on the weight of the carrier. In a particular embodiment, the amount of magnesium stearate is 0.1% w/w, based on the weight of the carrier.

In other embodiments, the amount of magnesium stearate will depend on the particle size and hence on the surface area of the carrier particles.

For example, with carrier particles having a great surface area such those having small particle size, e.g. 60 to 90 microns, the amount of magnesium stearate will be preferably 0.65 to 1.25% w/w, while with carrier particles having a smaller surface area such those having a bigger particle size, e.g. 90 to 150 microns, the amount will be preferably 0.1 to 0.3% w/w.

The lactose particles may be any type of crystalline lactose or mixture thereof. Advantageously, the lactose particles are made of alpha-lactose or beta-lactose or solvates thereof. Preferably, the carrier particles are particles of alpha-lactose monohydrate.

All of the lactose particles have a mass diameter in the range of 30 to 1000 microns. Particles having a mass diameter of 50 to 500 microns may be advantageously used. In a preferred embodiment, the mass diameter is 60 to 200 microns. In particular embodiments, particles having a mass diameter of 60 to 90 microns or 90 to 150 microns may be used. In other embodiments, the mass diameter is 150 to 400 microns or 210 to 355 microns.

The size of the carrier particles is an important factor in the efficiency of the inhaler. The desired particle size may be obtained by sieving.

In a particularly preferred embodiment, the particle size distribution fulfils the following parameters: d(v0.1) of 85 to 100 microns, d(v0.5) of 125 to 135 microns, and d(v0.9) of 180 to 190 microns.

The lactose particles are subjected to dry-coating with magnesium stearate particles until the extent of surface coating is higher than 60%, advantageously equal to or higher than 70%, more advantageously of at least 80%, preferably equal to or higher than 85%, more preferably equal to or higher than 90%, even more preferably equal to or higher than 95%. Under particular conditions, it might be possible to achieve a surface coating of 100%. Although it may be possible to achieve a surface coating of 100%, a lower percentage of surface area coating may be a more practical upper limit, such as 99.9%, 99%, 98%, 97%, or 96%.

The extent to which magnesium stearate coats the surface of the lactose particles may be determined by first measuring the water contact angle, and then applying the equation known in the literature as Cassie and Baxter, cited at page 338 of Colombo I et al., *Il Farmaco*, 1984, 39(10), pp. 328-341, which is incorporated herein by reference in its entirety, and reported below.

$$\cos \theta_{mixture} = f_{MgSt} \cos \theta_{MgSt} + f_{lactose} \cos \theta_{lactose}$$

where $f_{MgSt}$ and $f_{lactose}$ are the surface area fractions of magnesium stearate and of lactose;

$\theta_{MgSt}$ is the water contact angle of magnesium stearate;

$\theta_{lactose}$ is the water contact angle of lactose; and $\theta_{mixture}$ are the experimental contact angle values.

The measure of the contact angle between a liquid and a solid surface is commonly used in the art for determining the wettability of solids. This approach is based on the capability of a liquid to spread spontaneously over the surface of a solid to reach a thermodynamic equilibrium.

For the purpose of the present invention, the contact angle may be determined with methods that are essentially based on goniometric measurements. These imply the direct observation of the angle formed between the solid substrate and the liquid under testing. It is therefore quite simple to carry out, being the only limitation related to possible bias stemming from intra-operator variability. It should be, however, underlined that this drawback can be overcome by adopting a fully automated procedure, such as a computer assisted image analysis.

A particularly useful approach is the sessile or static drop method as referenced on page 332 of Colombo et al. (ibidem), that is carried out by depositing a liquid drop onto the surface of the powder in the form of a disc obtained by compaction (compressed powder disc method).

Typically, the procedure is carried out as follows:
The compressed disc is prepared by adding the sample into the die of a press and a compression force of 5 kN is applied for 3 minutes. Then the compressed disc is placed on a plate of a surface wettability tester and a water drop of about 10:1 is formed on the surface of the disc.

A suitable surface wettability tester is, for example, that available from Lorentzen & Wettre GmbH.

The pictures are taken with a videocamera and the water contact angles values are given by a computer assisting in the analysis of the image.

If a fully automated procedure is not available, the base (b) and the height (h) of the drop are measured on the display using a mobile reading scale, then the water contact angles (WCA) are calculated by applying the following formula:

$$WCA=[arctg2h/b] \times 2 \times 180/B$$

Typically the values are calculated as a mean of three different measurements taken at room temperature. The precision is usually of about ±5°.

The extent to which the magnesium stearate coats the surface of the lactose particles may also be determined by X-ray photoelectron spectroscopy (XPS), a well known tool for determining the extent as well as the uniformity of distribution of certain elements on the surface of other substances. In the XPS instrument, photons of a specific energy are used to excite the electronic states of atoms below the surface of the sample. Electrons ejected from the surface are energy filtered via a hemispherical analyser (HSA) before the intensity for a defined energy is recorded by a detector. Since core level electrons in solid-state atoms are quantized, the resulting energy spectra exhibit resonance peaks characteristic of the electronic structure for atoms at the sample surface.

Typically XPS measurements are taken on an Axis-Ultra instrument available from Kratos Analytical (Manchester, UK) using monochromated Al Kα radiation (1486.6 eV) operated at 15 mA emission current and 10 kV anode potential (150 W). A low energy electron flood gun is used to compensate for insulator charging. Survey scans, from which quantification of the detected elements are obtained, are acquired with analyser pass energy of 160 eV and a 1 eV step size. High-resolution scans of the C 1s, O 1s, Mg 2s, N 1s and Cl 2p regions are acquired with pass energy of 40 eV and a 0.1 eV step size. The area examined is approximately 700 μm×300 μm for the survey scans and a 110 μm diameter spot for the high-resolution scans.

In the context of the present invention, by XPS, it is possible to calculate both the extent of coating and the depth of the magnesium sterate film around the lactose particles. The extent of magnesium stearate (MgSt) coating is estimated using the following equation:

$$\% \text{ MgSt coating}=(\% \text{ Mg}_{sample}/\% \text{ Mg}_{ref}) \times 100$$

where
$Mg_{sample}$ is the amount of Mg in the analyzed mixture; and
$Mg_{ref}$ is the amount of mg in the reference sample of commercially available MgSt.

Usually the values are calculated as a mean of two different measurements. Typically, an accuracy of 10% is quoted for routinely performed XPS experiments.

XPS measurements may be taken with commercially available instruments such as Axis-Ultra instrument from Kratos Analytical (Manchester UK), typically using monochromated Al K∀ radiation according to known procedures.

Within the limits of the experimental error, a good consistency has been found between the extent of coating as determined by XPS measurements and that as estimated by the theoretical calculations based on the Cassie and Baxter equation.

Another analytical technique that may advantageously be used for determining the extent of coating is scanning electron microscopy (SEM).

Such microscopy may be equipped with an EDX analyzer (an Electron Dispersive X-ray analyzer), that can produce an image selective to certain types of atoms, for example magnesium atoms. In this manner it is possible to obtain a clear data set on the distribution of magnesium stearate on the surface of carrier particles.

SEM may alternatively be combined with IR or Raman spectroscopy for determining the extent of coating, according to known procedures.

The apparatus in which the process of the invention is carried out should be a high shear mixer granulator based on friction, operating at a rotation speed equal to or higher than 500 r.p.m., but equal to or lower than 2500 r.p.m, preferably between 500 and 2000 r.p.m., more preferably 1000 to 1500 r.p.m.

It has indeed been found that, if the carrier particles have a mass diameter equal to or higher than 90 microns, at a rotation speed of 2000 r.p.m., the particles of lactose begin to break, and hence a significant reduction of the particle size is observed.

A typical high shear mixer granulator which can be employed for carrying out the process of the invention is the CYCLOMIX™ apparatus (Hosokawa Micron Group Ltd).

Said apparatus comprises a stationary conical vessel fitted with paddle-shaped mixing elements, which rotate close to the inner vessel wall.

The powder loaded into the conical mixing vessel from the top; the degree of filling can range between 30 and 100%. Together, the rotation of the paddles and the conical shape of the vessel force the powder from the bottom to the upper zone of the vessel. Upon reaching the top, the powder flows downwards into the centre of the vessel. This flow pattern results in fast macromixing. During the upward motion, the particles of the powder are accelerated by the paddles and intensively mixed by friction with vessel. Such effects are sufficient to soften, break, distort, flatten, and wrap the particles of magnesium stearate around the carrier particles to form a coating.

The product temperature remained constant during all the experiments. However, the temperature may be controlled in an accurate and reliable way.

When the process is carried within the claimed limits in terms of rotation speed, the particle size of the lactose particles remains substantially the same and a high extent of coating is achieved.

However, if lactose particles substantially rid of fine lactose particles are desired, the rotation speed would be preferably maintained equal to or lower than 1500 r.p.m., i.e. between 1000 and 1500 r.p.m., whereas at higher rotating speeds it would be possible to produce in situ a small percentage of fine carrier particles as reported for example in WO 00/53158.

Typically a fraction of not more than 10% of fine particles can be produced with a MMD lower than 20 microns, preferably lower than 10 microns.

It would be preferable anyway to provide carrier particles made of lactose coated with magnesium stearate rid of fine lactose particles.

The time of processing depends of the type of carrier particles and on the size of the batch and shall be adjusted by the skilled person.

Apparatus with a capacity up to 500 liters are presently available on the market.

Typically, the time of processing is 1 to 30 minutes, preferably 2 to 20 minutes, more preferably 5 to 15 minutes.

In some embodiments, the time of processing is about 10 minutes.

The time of processing would also affect the extent of coating and it would be adjusted by the skilled person depending on the amount of magnesium stearate employed and the extent of coating desired.

Carriers obtainable by the process of the present invention exhibit good flow properties, as they have a Carr's index well below the value of 25, which is usually taken as a discriminating value for free flowing powders.

Carr's index is calculated by applying the following formula:

$$\text{Carr's index} = \frac{ds - dv}{ds} \times 100$$

where:
dv is the poured density; and
ds is the tapped density.

The densities were calculated according to the method reported as follows.

Powder mixtures (about 70 g) were poured into a glass graduated cylinder and the unsettled apparent volume $V_0$ was read; the apparent density before settling (poured density, dv) was calculated dividing the weight of the sample by the volume $V_0$. After 1250 taps with the described apparatus, the apparent volume after settling ($V_{1250}$) was read and the apparent density after settling (tapped density, ds) was calculated.

Since the flow properties of the carrier are good, it follows that the flow properties of the corresponding pharmaceutical formulations in form of dry powders are good.

The pharmaceutical formulations comprising the carrier of the present invention also show good aerosol performance in terms of respirable fraction and significantly higher aerosol performances than formulations comprising a carrier prepared according to U.S. Pat. No. 6,528,096.

Moreover, the percentage of respirable magnesium stearate particles delivered by the carrier of the invention is significant lower that the percentage delivered by the carrier of the prior art. This indicates that said additive adheres more strongly to the surface of the carrier particles, it is released much less from the carrier of the present invention during inhalation, and it is hence less available for systemic absorption.

The formulations comprising the carrier of the present invention also turned out to be physically stable in the device before use.

Finally, due to increase of the their hydrophobic properties, the carrier particles of the present invention tend to adsorb less water as demonstrated by the dynamic vapor sorption experiments, making them particularly useful for preparing dry powder formulations comprising hydrophobic and/or hydrophilic active ingredients.

Accordingly, the present invention provides pharmaceutical compositions in the form of a dry powder for inhalation comprising the carrier particles of the present invention and one or more active ingredients.

The active ingredient may be practically any pharmaceutically active compound which can be administered by inhalation of a dry powder.

As an example, they may be chosen from short-acting and long-acting beta$_2$-agonists such as terbutalin, reproterol, salbutamol, salmeterol, formoterol, carmoterol, milveterol, indacaterol, olodaterol, fenoterol, clenbuterol, bambuterol, broxaterol, epinephrin, isoprenaline or hexoprenaline or salts and/or solvate forms thereof; short-acting and long-acting anticholinergics such as tiotropium, ipratropium, oxitropium, oxybutynin, aclidinium, trospium, glycopyrronium, or the compounds known with the codes GSK 573719 and GSK 1160274, in form of salts and/or solvate forms thereof; bifunctional Muscarinic Antagonist-beta2 Agonist (MABA) compounds for inhalation such as GSK 961081; short-acting and long acting corticosteroids such as butixocart, rofleponide, flunisolide budesonide, ciclesonide, mometasone and its ester, i.e. furoate, fluticasone and its ester, i.e. propionate and fuorate, beclomethasone and its ester, i.e. propionate, loteprednol or triamcinolone acetonide and solvate forms thereof; leukotrien-antagonists, such as andolast, iralukast, pranlukast, imitrodast, seratrodast, zileuton, zafirlukast or montelukast; phosphodiesterase-inhibitors, such as filaminast, piclamilast or roflumilast; an PAF-Inhibitor, such as apafant, rorapafant or israpafant; pain killers such as morphine, fentanyl, pentazocine, buprenorphine, pethidine, tilidine, or methadone; potency agents such as sildenafil, alprostadil or phentolamine; or a pharmaceutically acceptable derivative or salt of any of the foregoing compounds or classes of compounds. In as much as any of these compounds possess chiral centers, the compounds can be used in optically pure form, or can be presented as diastereomeric mixtures or racemic mixtures.

Dry powder formulations of the present invention may also employ proteins, peptides, oligopeptides, polypeptides, polyamino acids nucleic acid, polynucleotides, oligonucleotides, and high molecular weight polysaccharides.

Examples of macromolecules that find use in the present invention are: albumins (preferably, human serum Insulin; albumin); BSA; IgG; IgM; insulin; GCSF; GMCSF; LHRH; VEGF; hGH; lysozyme; alpha-lactoglobulin; basic fibroblast growth factor basic fibroblast growth factor; (bFGF); asparaginase; urokinase-VEGF; chymotrypsin; trypsin; streptokinase; interferon; carbonic anhydrase; ovalbumin; glucagon; ACTH; oxytocin; phosphorylase b; alkaline phosphatase-secretin; vasopressin; levothyroxin; phatase; beta-galactosidase; parathyroid hormone, calcitonin; fibrinogen; polyaminoacids (e.g., DNAse, alphal antitrypsin; polylysine, polyarginine); angiogenesis inhibitors or pro-immunoglobulins (e.g., antibodies); somatostatin and analogs; casein; collagen; gelatin; soy protein; and cytokines (e.g., interferon, interleukin); immunoglobulins; physiologically active proteins such as peptide hormones, cytokines, growth factors, factors acting on the cardiovascular system, factors acting on the central and peripheral nervous systems, factors acting on humoral electrolytes and hemal substances, factors acting on bone and skeleton, factors acting on the gastrointestinal system, factors acting on the immune system, factors acting on the respiratory system, factors acting on the genital organs, and enzymes; hormones and hormone modulators including insulin, proinsulin, C-peptide of insulin, growth hormone, parathyroid hormone, luteinizing hormone-releasing hormone (LH-RH), adrenocorticotropic hormone (ACTH), amylin, oxytocin, luteinizing hormone, (D-Tryp6)-LHRH, nafarelin acetate, leuprolide acetate, follicle stimulating hormone, glucagon, prostaglandins, estradiols, testosterone, and other factors acting on the genital organs and their derivatives, analogues and congeners. As analogues of said LH-RH, known substances described for instance in U.S. Pat. Nos. 4,008,209, 4,086,219, 4,124,577, 4,317,815 and 5,110,904, which are incorporated herein by reference in their entireties, can be mentioned; hematopoietic or thrombopoietic factors include, among others, erythropoietin, granulocyte colony stimulating factor (G-CSF), granulocyte-macrophage stimulating factor (GM-CSF) and macrophage colony stimulating factor (M-CSF), leukocyte proliferation factor preparation, thrombopoietin, platelet proliferation stimulating factor, megakaryocyte proliferation (stimulating) factor, and factor VIII; enzymes and enzyme cofactors including pancrease, L-asparaginase, hyaluronidase, chymotrypsin, trypsin, streptokinase, urokinase, pancreatin, collagenase, trypsinogen, chymotrypsinogen, plasminogen, streptokinase, adenyl cyclase, and superoxide dismutase (SOD); vaccines include Hepatitis B, MMR (measles, mumps, and rubella), and Polio vaccines; growth factors include nerve growth factors (NGF, NGF-2/NT-3), epidermal growth factor (EGF), fibroblast growth factor (FGF), insulin-like growth factor (IGF), transforming growth factor (TGF), platelet-derived cell growth factor (PDGF), and hepatocyte growth factor (HGF); factors acting on the cardiovascular system including factors which control blood pressure, arteriosclerosis, etc, such as endothelins, endothelin inhibitors, endothelin antagonists, endothelin producing enzyme inhibitors vasopressin, renin, angiotensin I, angiotensin 11, angiotensin III, angiotensin I inhibitor, angiotensin II receptor antagonist, atrial natriuretic peptide (ANP), and antiarrythmic peptide; factors acting on the central and peripheral nervous systems including opioid peptides (e.g. enkephalins, endorphins), neurotropic factor (NTF), calcitonin gene-related peptide (CGRP), thyroid hormone releasing hormone (TRH), salts and derivatives of, and neurotensin; factors acting on the gastrointestinal system including secretin and gastrin; factors acting on humoral electrolytes and hemal substances including factors which control hemagglutination, plasma cholesterol level or metal ion concentrations, such as calcitonin, apoprotein E and hirudin. Laminin and intercellular adhesion molecule 1 (ICAM 1) represent exemplary cell adhesion factors; factors acting on the kidney and urinary tract including substances which regulate the function of the kidney, such as brain-derived natriuretic peptide (BNP), and urotensin; factors which act on the sense organs including factors which control the sensitivity of the various organs, such as substance P; chemotherapeutic agents, such as paclitaxel, mytomycin C, and doxorubicin; factors acting on the immune system including factors which control inflammation and malignant neoplasms and factors which attack infective microorganisms, such as chemotactic peptides; and naturally occurring, chemically synthesized or recombinant peptides or proteins which may act as antigens, such as cedar pollen and ragweed pollen, and these materials alone, or together, or coupled with haptens, or together with an adjuvant.

Formulations comprising a beta$_2$-agonist, an anti-cholinergic or a corticosteroid for inhalation, alone or in any combination thereof, constitute particular embodiments of the invention.

These actives may be present in a particular salt and/or solvate form thereof, such as beta$_2$-agonists, e.g. formoterol fumarate dihydrate, salbutamol sulphate, salmeterol xinafoate, milveterol hydrochloride, and indacaterol maleate; anti-cholinergics, e.g. as glycopyrronium bromide in form of (3R,2R') enantiomer or racemic mixture (3S,2R') and (3R, 2S'), tiotropium bromide, oxytropium bromide, ipratropium bromide, oxybutynin chloride, aclidinium bromide, or trospium chloride.

The corticosteroids for inhalation instead may be present in a particular ester form and/or solvate form thereof, e.g. beclomethasone dipropionate or its monohydrate form, fluticasone propionate, fluticasone furoate, or mometasone furoate.

In a particular embodiment, formulations comprising the dihydrate form of formoterol fumarate and its combinations with corticosteroids for inhalation and/or anticholinergics are preferred.

In another particular embodiment, a salt of vilanterol or indacaterol and combinations thereof with corticosteroids for inhalation and/or anticholinergics are preferred.

In order that the active substance is inhalable, i.e. it can pass into the deep lung such as the terminal and respiratory bronchioles and the alveolar ducts and sacs, it must be in particulate form having a mean particle diameter (measured as the mass mean diameter) of at most about 10 microns, e.g. from 1 to 10 microns, and preferably 1 to 6 microns. Such microfine particles may be obtained in a manner known per se, for example by micronization, controlled precipitation from selected solvents, spray drying, supercritical fluids, or according to the processes described in WO 2004/073827, WO 2008/155570, WO 2008/114052 and WO 2010/007447, which are incorporated herein by reference in their entireties.

The therapeutically amount of the active substance may vary within wide limits depending on the nature of the active substance, the type and severity of the condition to be treated, and the condition of the patient in need of treatment.

Typically the active substance particles are added to the carrier particles of the invention by mixing. The particles may be mixed using a tumbling blender (for example a Turbula mixer) according to procedures known in the art.

In particular, the rotation speed of the mixer and the time of mixing shall be adjusted by the skilled person to obtain a good uniformity of distribution of the active ingredient in the formulation.

An excellent uniformity of distribution of the active ingredient is achieved when the active ingredient has a particle size distribution wherein no more than 10% of the particles have a volume diameter [d(v,0.1)] lower than 0.8 microns, preferably of lower than 0.9 microns, more preferably lower than 1 micron, and no more than 50% of particles have a volume diameter [d(v,0.5)] lower than 1.7 microns preferably lower than 1.9 microns, more preferably lower than 2 microns.

The dry powder formulation for inhalation comprising the carrier particles of the present invention may be utilized with any dry powder inhaler.

Dry powder inhalers can mainly be divided into: i) single-dose (unit-dose) inhalers, for the administration of single subdivided doses of the active compound; and ii) pre-metered multi-dose inhalers or reservoir inhalers pre-loaded with quantities of active principles sufficient for longer treatment cycles.

The dry powder formulations may be presented in unit dosage form. Dry powder compositions for topical delivery to the lung by inhalation may, for example, be presented in capsules and cartridges of for example gelatin, or blisters of for example laminated aluminium foil, for use in an inhaler or an insufflator.

The dry powder formulation for inhalation according to the present invention is particularly suitable for multi-dose dry powder inhalers comprising a reservoir from which individual therapeutic dosages can be withdrawn on demand through actuation of the device.

A preferred multi-dose device is the inhaler described in WO 2004/012801, which is incorporated herein by reference in its entirety.

Other multi-dose devices that may be used are for instance the DISKUS™ of GlaxoSmithKline, the TURBOHALER™ of AstraZeneca, TWISTHALER™ of Schering, and CLICKHALER™ of Innovata.

As marketed examples of single-dose devices, there may be mentioned ROTOHALER™ of GlaxoSmithKline and HANDIHALER™ of Boehringer Ingelheim.

Other features of the invention will become apparent in the course of the following descriptions of exemplary embodiments which are given for illustration of the invention and are not intended to be limiting thereof.

i) the crystallinity by powder X-ray diffractometry (XRD);

ii) determination of the magnesium stearate in the powder by thermogravimetric-differential scanning calorimetry (ATG-DSC) measurements and by Fourier-Transformed-Infra Red (FT-IR) analysis;

iii) the surface aspect by scanning electron microscope (SEM);

iv) the particle size distribution (PSD) by laser diffraction with a Malvern apparatus; the water contact angle by the sessile drop method wherein the powder is in the form of a disc obtained by compaction (compressed powder disc method) according to the procedure reported above in the description;

v) the water adsorption at increasing percentage of relative humidity by dynamic vapor sorption (DVS) experiments; and vi) the flow properties (flowability) by determining the Can index.

The list of the experiments that were carried out is reported in Table 1.

TABLE 1

List of the experiments that were carried out.

| C MgSt (%) | Rotation Speed (rpm) | Time (min) | PSD | SEM | Flowability | Sessile drop | DSC | FTIF | DVS | XRD |
|---|---|---|---|---|---|---|---|---|---|---|
| 0 | — | — | x | x |  | x | x | x | x | x |
| 0 | 1000 | 5 | x | x | x | x |  |  |  |  |
| 0 | 1000 | 10 | x | x | x | x |  |  |  |  |
| 0 | 1000 | 15 | x | x | x | x |  |  |  |  |
| 0 | 1500 | 5 | x | x | x | x |  |  | x |  |
| 0 | 1500 | 10 | x | x | x | x |  |  | x |  |
| 0 | 1500 | 15 | x | x | x | x |  |  | x | x |
| 0 | 2000 | 15 | x | x | x |  |  |  |  |  |
| 0.5 | — | — | x | x | x | x | x | x |  |  |
| 0.5 | 1000 | 5 | x | x | x | x |  | x |  |  |
| 0.5 | 1000 | 10 | x | x | x | x |  | x |  |  |
| 0.5 | 1000 | 15 | x | x | x | x |  | x |  |  |
| 0.5 | 1500 | 5 | x | x | x | x |  | x |  |  |
| 0.5 | 1500 | 10 | x | x | x | x |  | x |  |  |
| 0.5 | 1500 | 15 | x | x | x | x |  | x | x | x |
| 100 | — |  |  |  |  | x | x | x | x |  |

EXAMPLES

Example 1

Preparation of the Carrier; Study of the Processing Conditions

Alpha-lactose monohydrate commercially available was sieved to give a sample having particles with a range of diameter from 90 to 150:m. About 450 g of said alpha-lactose monohydrate mixed with 0.5% w/w of magnesium stearate was fed into the stationary conical vessel of a 1 liter laboratory model CYCLOMIX™ apparatus (Hosokawa Micron Ltd). The process was conducted using varying different parameters (rotation speed, processing time). Alpha-lactose monohydrate and a mixture of alpha-lactose monohydrate and 0.5% magnesium stearate processed at 2000 r.p.m. for 15 minutes were also processed for comparative purposes. The obtained particles were collected and subjected to chemico-physical technological characterization.

In particular, the following characteristics were determined:

Example 2

Results of the Characterization of the Formulations of Example 1

The XRD analysis carried out on the sample obtained under the more stressing conditions (1500 r.p.m. for 15 minutes) among those tested, indicates that lactose remains crystalline. The marker band at 2850 cm$^{-1}$ in the FT-IR spectrum also confirms the presence in the samples of magnesium stearate. Representative SEM pictures are reported in FIG. 2. From the images it can be appreciated that the treatment of carrier particles mixed with 0.5 w/w magnesium stearate at 1500 r.p.m for 5, 10, and 15 minutes does not substantially change the particle size. The same was observed for a rotation speed of 1000 r.p.m. (data not shown). On the contrary, at 2000 r.p.m. the particles of lactose begin to break, and a reduction of the particle size is observed together with the production of a significant amount of fine particles.

The findings are confirmed by the results of the PSD analysis reported in Table 2. The results are expresses as mean of three determinations. In Table 2, the water contact angle values and the corresponding extent of surface coating calculated from the Cassie and Baxter equation are also reported. Said equation was applied to the experimental values of the penultimate column of Table 2 using the reference values for magnesium state alone and alpha-lactose monohydrate alone. The variability in terms of S.D. of the experimental values is always less than ±10%, typically of ±5%.

Figure 3:
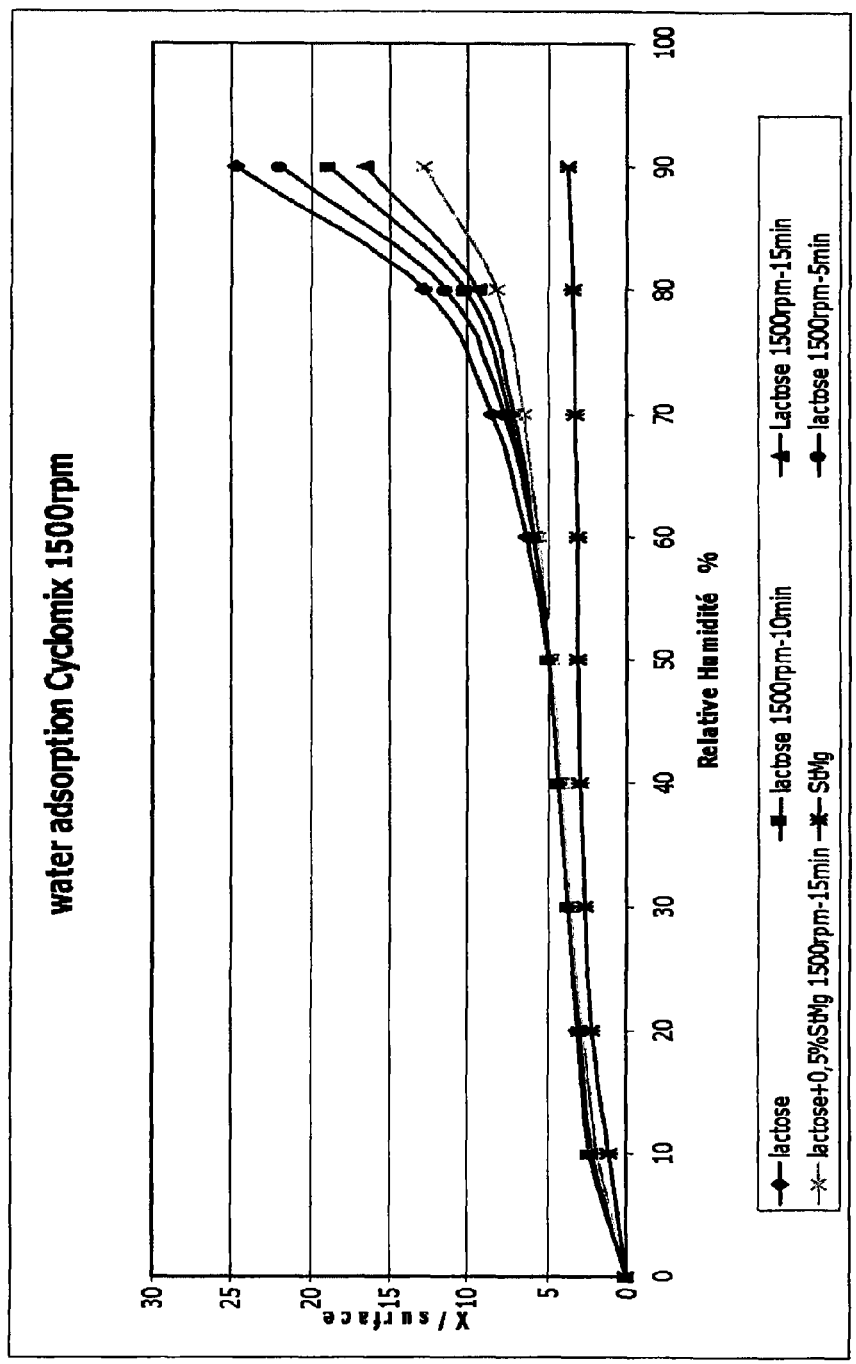
FIG. 3 is a graph which shows water adsorption at increasing percentage of relative humidity.

The results show that the extent of surface coating is always higher than 85%. Moreover, from the DVS experiments, it can be appreciated that the increased hydrophobicity of the carrier particles coated with magnesium stearate in comparison to those of lactose make them less prone to adsorb water from the environmental moisture (see, FIG. 3).

TABLE 2

PSD analysis and water contact angle determination.

| Rotation speed (r.p.m.) | Time (minutes) | PSD d(v0.1) | PSD d(v0.5) | PSD d(v0.9) | Water Contact Angle (E) | Extent of Surface Coating (%) |
|---|---|---|---|---|---|---|
| α-lactose mono-hydrate | — | 96.4 | 132.2 | 182.3 | 8.35 | 0 |
| 1000 | 5 | 96.7 | 132.7 | 182.6 | 121.50 | 89.6 |
| 1000 | 10 | 96.1 | 132.3 | 182.4 | 116.50 | 85.1 |
| 1000 | 15 | 96.2 | 132.4 | 182.4 | 123.70 | 91.5 |
| 1500 | 5 | 95.5 | 131.6 | 180.9 | 135.62 | 100 |
| 1500 | 10 | 96.4 | 132.4 | 181.9 | 134.52 | 100 |
| 1500 | 15 | 95.4 | 131.2 | 179.9 | 127.13 | 94.4 |

Reference value for the water contact angle of magnesium stearate alone: 134.30°
Reference value for the water contact angle of α-lactose monohydrate alone: 8.35°

The values of the densities and the corresponding Carr's index for 5, 10, and 15 minutes are reported in Table 3.

TABLE 3

Densities and corresponding Carr's index.

| Rotation speed (r.p.m.) | Time (minutes) | dv (g cm$^{-1}$) | ds (g cm$^{-1}$) | Carr's Index |
|---|---|---|---|---|
| 1000 | 5 | 0.779 | 0.835 | 6.7 |
| 1000 | 10 | 0.776 | 0.825 | 5.9 |
| 1000 | 15 | 0.770 | 0.835 | 7.8 |
| 1500 | 5 | 0.775 | 0.840 | 7.7 |
| 1500 | 10 | 0.770 | 0.830 | 7.2 |
| 1500 | 15 | 0.762 | 0.825 | 7.6 |

All the samples exhibits good flow properties as they have a Carr's index of 5 to nd hence well below the value of 25, which is usually taken as discriminating value.

Example 3

Preparation of Other Carriers

Carries according to the present invention are prepared as described in Example 1, but by mixing alpha-lactose monohydrate with 0.3% w/w magnesium stearate at 1000 r.p.m., and with 0.5% w/w magnesium stearate at 500 r.p.m., at different times of mixing. The obtained samples are subjected to particle size distribution, flowability determination, and water contact angle determination. The results of the water contact angles determination are reported in Table 4.

TABLE 4

Water contact angles.

| Rotation speed (r.p.m.) | Time (minutes) | MgSt amount (% w/w) | Contact angle (°) | Extent of coating (%) |
|---|---|---|---|---|
| 1000 | 10 | 0.3 | 95 | 64 |
| 1000 | 15 | 0.3 | 100 | 69 |
| 500 | 5 | 0.5 | 110 | 79 |
| 500 | 10 | 0.5 | 110 | 79 |
| 500 | 15 | 0.5 | 115 | 84 |

Example 4

Inhalable Dry Powder BDP Formulations Comprising the Carrier of the Present Invention The carriers were prepared as described in Examples 1 and 3 at a rotation speed of 1000 r.p.m. for 15 minutes. Micronized beclomethasone dipropionate is obtained by conventional jet mill micronization. A powder formulation according to the invention is prepared with the composition reported in Table 5.

TABLE 5

BDP dry powder formulation 1.

| | Amounts | | |
|---|---|---|---|
| | Per shot of the inhaler | | Single dose |
| Components | Mg | % | microgram |
| Beclomethasone dipropionate (BDP) | 0.100 | 1.0 | 100 |
| Alpha-lactose monohydrate 90 to 150 microns | 9.85 | 98.5 | |
| Magnesium stearate | 0.05 | 0.5 | |
| Total weight | 10 | | |

The final formulation is filled in the multidose dry powder inhaler described in WO 2004/012801, which is incorporated herein by reference in its entirety.

Further powder formulations according to the present invention are prepared with the compositions reported in Tables 6 and 7.

TABLE 6

BDP dry powder formulation 2.

| | Amounts | | |
|---|---|---|---|
| | Per shot of the inhaler | | Single dose |
| Components | Mg | % | microgram |
| Beclomethasone dipropionate (BDP) | 0.100 | 1.0 | 100 |
| alpha-lactose monohydrate 90 to 50 microns | 9.89 | 98.9 | |
| Magnesium stearate | 0.01 | 0.1 | |
| Total weight | 10 | | |

TABLE 7

BDP dry powder formulation 3.

| | Amounts | | |
|---|---|---|---|
| | Per shot of the inhaler | | Single dose |
| Components | mg | % | microgram |
| Beclomethasone dipropionate (BDP) | 0.100 | 1.0 | 100 |
| alpha-lactose monohydrate 90 to 150 microns | 9.87 | 98.7 | |
| Magnesium stearate | 0.03 | 0.3 | |
| Total weight | 10 | | |

The aerosol performances of said formulations were evaluated using a Multi Stage Liquid Impinger (MSLI) according to the procedure described in European Pharmacopoeia $2^{nd}$ edition, 1995, part V.5.9.1, pages 15-17, which is incorporated herein by reference. The results in terms of delivered dose (DD), fine particle mass (FPM), fine particle fraction (FPF), and mass median aerodynamic diameter (MMAD), are reported in Table 8 (mean of three determinations±S.D.).

TABLE 8

Aerosol performances.

| Formulation | DD (:g) | FPM (:g) | FPF (%) | MMAD (:m) |
|---|---|---|---|---|
| BDP 1 | 109.2 ± 2.5 | 41.7 ± 7.1 | 48.4 ± 2.2 | 1.99 ± 0.14 |
| BDP 2 | 101.1 ± 5.9 | 29.9 ± 1.9 | 37.6 ± 6.8 | 1.80 ± 0.42 |
| BDP 3 | 109.9 ± 3.1 | 30.4 ± 2.0 | 34.1 ± 0.5 | 2.20 ± 0.15 |

The FPF, which is an index of the respirable fraction, turned out to be excellent, indicating that the formulations comprising the carriers of the invention are capable of providing good aerosol performances. Said formulations also gave rise to significantly higher FPF in comparison to analogous formulations comprising a carrier prepared by mixing by mixing alpha-lactose monohydrate and magnesium stearate in a Turbula mixer at 32 r.p.m. for 120 minutes, according to U.S. Pat. No. 6,528,096.

Example 5

Inhalable Dry Powder Formulation Comprising Formoterol Fumarate the Carrier of the Present Invention The carrier was prepared as described in Example 1 at a rotation speed of 1000 r.p.m. for 10 minutes. Micronized formoterol fumarate dihydrate was obtained by conventional jet mill micronization. A powder formulation according to the invention was prepared with the composition reported in Table 9. The final formulation was filled in the multidose dry powder inhaler described in WO 2004/012801, which is incorporated herein by reference in its entirety.

TABLE 9

Formoterol fumarate (FF) dry powder formulation 1.

| | Amounts | | |
|---|---|---|---|
| | Per shot of the inhaler | | Single dose |
| Components | mg | % | microgram |
| Formoterol fumarate dehydrate | 0.0012 | 0.12 | 12 |
| Alpha-lactose monohydrate 90 to 150 microns | 9.948 | 99.48 | |
| Magnesium stearate | 0.05 | 0.5 | |
| Total weight | 10 | | |

The aerosol performances of said formulations were evaluated using a Multi Stage Liquid Impinger (MSLI) according to the procedure described in European Pharmacopoeia $2^{nd}$ edition, 1995, part V.5.9.1, pages 15-17, which is incorporated here in by reference. The results in terms of delivered dose (DD), fine particle mass (FPM), fine particle fraction (FPF) and mass median aerodynamic diameter (MMAD), are reported in Table 10 (mean of three determinations±S.D.).

TABLE 10

Aerosol performances.

| Formulation | DD (:g) | FPM (:g) | FPF (%) | MMAD (:g) |
|---|---|---|---|---|
| FF 1 | 9.2 ± 0.9 | 2.4 ± 0.1 | 32.1 ± 4.5 | 1.52 ± 0.20 |

The FPF turned out to be satisfactory.

Said formulation also gave rise to significantly higher FPF in comparison to an analogous formulation comprising a carrier prepared by mixing by mixing alpha-lactose monohydrate and magnesium stearate in a Turbula mixer at 32 r.p.m. for 120 minutes, according to U.S. Pat. No. 6,528,096.

Example 6

Inhalable Dry Powder Comprising Formoterol Fumarate+BDP Formulation and the Carrier of the Invention A carrier is prepared as described in Example 1 at a rotation speed of 1000 r.p.m. for 15 minutes. Micronized beclomethasone dipropionate and formoterol fumarate dihydrate are obtained by conventional milling. A powder formulation according to the invention is prepared with the composition reported in Table 11. The final formulation is filled in the multidose dry powder inhaler described in WO 2004/012801, which is incorporated herein by reference in its entirety.

TABLE 11

Formoterol fumarate + BDP dry powder formulation.

| | Amounts | | |
|---|---|---|---|
| | Per shot of the inhaler | | Single dose |
| Components | mg | % | microgram |
| Formoterol fumarate dehydrate | 0.0006 | 0.06 | 6 |
| Beclomethasone dipropionate (BDP) | 0.100 | 1.0 | 100 |

TABLE 11-continued

Formoterol fumarate + BDP dry powder formulation.

| | Amounts | | |
|---|---|---|---|
| | Per shot of the inhaler | | Single dose |
| Components | mg | % | microgram |
| Alpha-lactose monohydrate 90 to 150 microns | 9.77 | 98.44 | |
| Magnesium stearate | 0.05 | 0.5 | |
| Total weight | 10 | | |

Example 7

Inhalable Dry Powder Formulation Comprising Glycopirronium Bromide and the Carrier of the Invention A carrier is prepared as described in Example 1 at a rotation speed of 1000 r.p.m. for 15 minutes. Micronized glycopyrronium bromide in the form of a racemic mixture (3S,2R') and (3R,2S') is obtained as described in WO 2010/007447, which is incorporated herein by reference in its entirety. A powder formulation according to the invention is prepared with the composition reported in Table 12. The final formulation is filled in the multidose dry powder inhaler described in WO 2004/012801, which is incorporated herein by reference in its entirety.

TABLE 12

Glycopyrronium bromide dry powder formulation.

| | Amounts | | |
|---|---|---|---|
| | Per shot of the inhaler | | Single dose |
| Components | mg | % | microgram |
| Glycopyrronium bromide | 0.05 | 0.5 | 50 |
| Alpha-lactose monohydrate 90 to 150 microns | 9.90 | 99.0 | |
| Magnesium stearate | 0.05 | 0.5 | |
| Total weight | 10 | | |

Example 8

Determination of the Respirable Fraction of Magnesium Stearate

The favorable properties of the carrier of the invention are illustrated by following experiment, where the release of Mg fine particles from a formulation thereof was investigated. Samples of carriers according to the invention as described in Example 1, prepared by mixing alpha-lactose monohydrate with 0.1% w/w, 0.3% w/w, or 0.5% w/w magnesium stearate in a CYCLOMIX™ apparatus at 1000 r.p.m. for 10 minutes were filled in the multidose dry powder inhaler described in WO 2004/012801, which is incorporated herein by reference in its entirety.

For sake of comparison, a blank as well as carriers prepared by mixing alpha-lactose monohydrate with 0.3% w/w or 0.5% w/w magnesium stearate in a Turbula mixer at 32 r.p.m. for 120 minutes, according to U.S. Pat. No. 6,528,096, were also prepared.

Micronized beclomethasone dipropionate (BDP) was added as reported in Example 4. The respirable fraction of magnesium stearate was evaluated using a Twin Stage Impinger apparatus (TSI, Copley Instruments Ltd, UK) according to the procedure described in the FU IX, $4^{th}$ Supplement, 1996 and applying a air flow of 60 l/minute. The limit value of the aerodynamic diameter ($d_{ae}$) for deposition in the lower separating chamber is 6.4 microns. Particles with larger $d_{ae}$ are deposited in Stage 1, while particles with smaller $d_{ae}$ in Stage 2. Ten doses of 15-18 mg were delivered for each experiment.

After aerosolization, the TSI apparatus was dismantled and the amounts of particles deposited in two separated chambers were harvested with a mixture of water:acetonitrile:HCl(2N) 40:40:20 v/v/v and brought up to a volume of 50 ml. The samples were calcinated in a microwave oven and the amount of Mg was determined by flame atomic absorption spectroscopy using a Perkin-Elmer instrument Analyst 800, according to standard procedures known in the art. The limit of detection (LOD) turned out to be 0.062 mg/ml.

The respirable fraction (FPF) of magnesium state was calculated by the ratio between the respirable dose and the delivered (emitted) dose. The delivered dose is calculated from the cumulative deposition in the apparatus, while the respirable dose is calculated from the deposition on Stages 2 corresponding to particles with a $d_{ae} \leq 6.4$ micron. The results are reported in Table 13 (mean±S.D.).

TABLE 13

Magnesium stearate respirable fraction.

| Sample | Mg (:g/ml) | MgSt in the sample (:g) | FPF MgSt (%) |
|---|---|---|---|
| Blank | <LOD | <LOD | — |
| Cyclomix MgSt 0.1% | <LOD | <LOD | 0 ± 0.0 |
| Cyclomix MgSt 0.3% | 0.08 ± 0.01 | 98 ± 15 | 15.7 ± 2.3 |
| Cyclomix MgSt 0.5% | 0.06 ± 0.00 | 85 ± 17 | 10.5 ± 1.5 |
| Turbula MgSt 0.3% | 0.123 ± 0.01 | 150 ± 14 | 32.3 ± 1.4 |
| Turbula MgSt 0.5% | 0.152 ± 0.01 | 171 ± 12 | 24.9 ± 1.2 |

Note:
P.M Mg = 24.31;
P.M. MgSt 591.24

As it can be appreciated, the percentage of respirable magnesium stearate particles delivered by the carrier of the present invention is significant lower that the percentage delivered by a comparative carrier. This indicates that said additive is released much less from the carrier of the present invention during inhalation, as it adheres more strongly to the surface of the carrier particles, and, hence, it is less available for systemic absorption.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A process for the preparation of a carrier for powder pharmaceutical compositions for inhalation, said process comprising dry coating lactose particles having a mass diameter of 30 to 1000 microns with 0.1 to 1.3% by weight, based on the weight of the carrier, of magnesium stearate, to obtain lactose particles surface coated with said magnesium stearate in an extent of more than 60% of the surface of said lactose particles, wherein said dry coating is carried out in a high shear mixer granulator based on friction behavior at a rotation speed equal of 500 r.p.m. to 2500 r.p.m.

2. A process according to claim 1, wherein said high shear mixer granulator is an apparatus fitted with paddle shape mixing elements wherein the particles are accelerated by the paddles and intensively mixed by the friction against the vessel wall.

3. A process according to claim 1, wherein said rotation speed is 1000 to 2000 r.p.m.

4. A process according to claim 2, wherein said rotation speed is 1000 to 2000 r.p.m.

5. A process according to claim 1, wherein said dry coating step is carried out for a time of 2 to 20 minutes.

6. A process according to claim 1, wherein said dry coating step is carried out for a time of 5 to 15 minutes.

7. A process according to claim 1, wherein at least 80% of the surface of said lactose particles is coated with said magnesium stearate.

8. A process according to claim 1, wherein at least 90% of the surface of said lactose particles is coated with said magnesium stearate.

9. Carrier particles for a dry powder pharmaceutical formulation, which are prepared by a process according to claim 1.

10. Carrier particles according to claim 9, wherein said rotation speed is 1000 to 2000 r.p.m.

11. A pharmaceutical composition in the form of a dry powder for inhalation, comprising carrier particles according to claim 9 and one or more active ingredients.

12. A pharmaceutical composition according to claim 11, wherein said active ingredient comprises at least one $beta_2$-agonist selected from the group consisting of salmeterol, formoterol, milveterol, vilanterol, olodaterol, indacaterol, a salt thereof, and a solvate form thereof.

13. A pharmaceutical composition according to claim 11, wherein said active ingredient comprises at least one anticholinergic selected from the group consisting of tiotropium bromide, ipratropium bromide, oxitropium bromide, oxybutynin chloride, aclidinium bromide, trospium chloride, glycopyrronium bromide, GSK 573719, and GSK 1160274.

14. A pharmaceutical composition according claim 11, wherein said active ingredient comprises at least one corticosteroid selected from the group consisting of beclomethasone dipropionate, fluticasone propionate, fluticasone furoate, budesonide, and mometasone furoate.

15. A pharmaceutical composition according to claim 11, wherein said active ingredient comprises a phosphodiesterase-inhibitor.

16. A dry powder inhaler, containing a pharmaceutical composition according to claim 11.

17. A method for the prevention and/or treatment of a respiratory, comprising administering to a subject in need thereof an effective amount of a pharmaceutical composition according to claim 11.

18. A method according to claim 17, wherein said respiratory conditions is asthma, chronic obstructive pulmonary disease, or allergic rhinitis.

* * * * *